United States Patent [19]

Chen

[11] Patent Number: 5,048,824
[45] Date of Patent: Sep. 17, 1991

[54] AIR RESISTANCE EXCERCISER WITH NEGATIVE ION GENERATOR

[75] Inventor: U-Fu Chen, Taipei, Taiwan
[73] Assignee: Ya Te Industry Co., Ltd., Taipei, Taiwan
[21] Appl. No.: 550,921
[22] Filed: Jul. 11, 1990
[51] Int. Cl.$^5$ ............................................. A63B 21/00
[52] U.S. Cl. ..................................... 272/116; 272/69; 272/72; 272/73; 434/247
[58] Field of Search ........................ 272/69, 72, 73, 93, 272/129, 132; 55/136, 139; 434/247, 392, 116; 128/25 R, 202.25, 787

[56] References Cited

U.S. PATENT DOCUMENTS

| 4,253,852 | 3/1981 | Adams | 55/136 X |
| 4,512,566 | 4/1985 | Bicocchi | 272/72 |
| 4,537,396 | 8/1985 | Hooper | 272/72 X |
| 4,589,656 | 5/1986 | Baldwin | 272/73 |
| 4,805,901 | 2/1989 | Kulick | 272/73 |
| 4,961,570 | 10/1990 | Chang | 272/73 |

Primary Examiner—Richard J. Apley
Assistant Examiner—Joe H. Cheng
Attorney, Agent, or Firm—Browdy and Neimark

[57] ABSTRACT

An air resistance exerciser with negative ion generator mainly includes an air resistance exerciser, a generator, a circuit board, and a ion generator. It is characterized by a small scale generator provided beside a blade wheel in the rotation mechanism of the exerciser at a proper position. When the blade wheel rotates and drives the generator to generate power, the power generated by the generator passes the circuit board and is voltage stabilizing and voltage increased to be used as the power source of the ion generator. The ion generator generates negative ions which combine with purified air to be discharged from the ion generator so that drifting dusts in the air can be minimized.

3 Claims, 5 Drawing Sheets

AIR RESISTANCE EXCERCISER WITH NEGATIVE ION GENERATOR

BACKGROUND OF THE INVENTION

Physical fitness equipments are important tools for modern people to maintain good health and fitness, and various fitness equipments are designed to meet different needs by different parts of human body. Presently commercially available air resistance exerciser are characterized by a large scale fan which is driven to rotate by force mechanically transformed from the energy generated by the user and provides exercise resistance through the rotation of blades thereon. For the users, a steadily increased resistance may be obtained from such air resistance exercises and, consequently, injuries occurred during exercise may be minimized, because the exercise resistance generated by such equipments varies with the rotation speed of the blades on the fan. It is therefore an obvious trend to use such fitness equipments.

However, the rotation of fan blades would inevitably stir the air flow in the room where the fitness equipment is located and used and therefore causes drifting dust in the air which degrades the cleanness of air and has reverse influence on the users who are using the equipments.

In view of this shortcoming existed in the conventional air resistance fitness equipments, the applicant then tried to develop based on his experiences over years an air resistance exerciser which is provided with a power generator on the fan rotation mechanism which is commonly possessed and needed by such type of exerciser. The rotation of this rotation mechanism may drive the power generator to generate electric power which flows through a circuit and is voltage stabilized and voltage increased to provide a voltage source for a set of ionizers. Negative ions are formed by this set of ionizers, then pass an air filter to filtrate dusts in air and deliver clean and negative-ions-contained air to the room, the health of the users is therefore protected.

SUMMARY OF THE INVENTION

It is a primary object of the present invention to provide an air resistance exerciser which may purify the room air by eliminating drifting dusts in the air caused by the rotation of fan blades on the equipment, and thereby further enhances the user's health.

A further object of the present invention is to provide an air resistance exercise which uses a power generator to generate electric power without additional power source.

BRIEF DESCRIPTION OF THE DRAWINGS

Other objects and advantages of the present invention will become apparent when referring to the following description and accompanying drawings wherein.

DETAILED DESCRIPTION OF PREFERRED EMBODIMENTS

Figure 1:
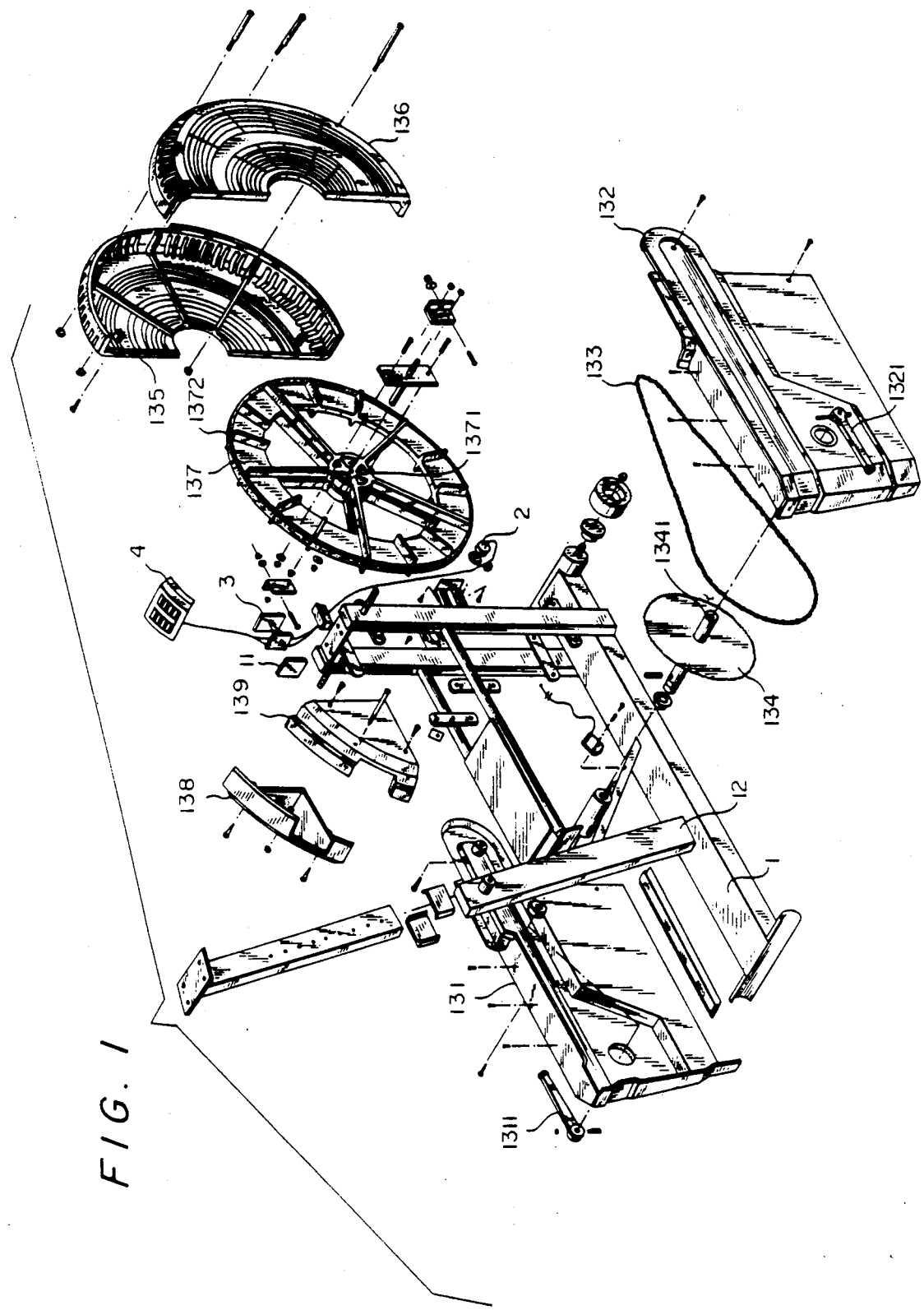
FIG. 1 is three-dimensional, analytical perspective of the invention.
Figure 2:
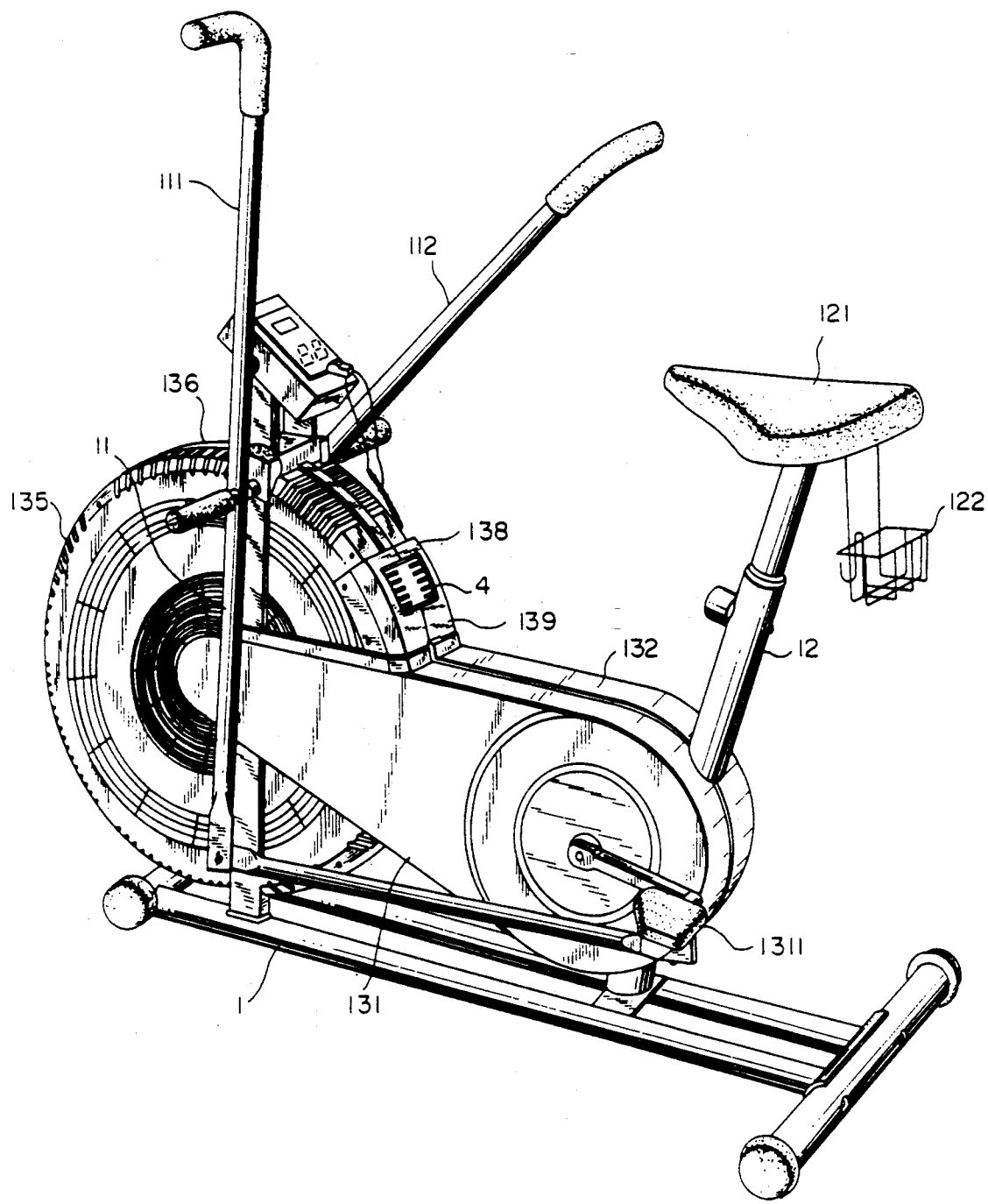
FIG. 2 is a three-dimensional perspective of the present invention showing it in an assembled condition.

Please refer to FIGS. 1 and 2 in which a bicycle type air resistance exercise with negative ion generator is shown.

On a base 1, a front frame 11 and a seat frame 12 are provided. The front frame 11 is upwardly extended to form two handle bars 111, 112; the seat frame 12 is upwardly extended to connect a saddle 121 with a towel rack 122 provided down behind the saddle 121. The height of saddle 121 is adjustable. A rotation mechanism is provided between the front frame 11 and seat frame 12 at a lower position and consists of a left protective cover 131, a right protective cover 132, a chain 133, a gear 134, two outer fan grills 135, 136, a blade wheel 137, two protective housings 138, 139, etc. The chain 133 is wound on and between the gear 134 and an axle 1371 of the blade wheel 137. An axle 1341 of the gear 134 transversely crosses the protective covers 131, 132 and projects out of two sides of the protective covers 131, 132 to connect two padals 1311, 1321 separately. The blade wheel 137 is covered by the outer fan grills 135, 136, and protective housings 138, 139, and is rotatable between two upstanding supports of the front frame 11. A user may sit on the saddle 121 with his (her) two hands holding on the two handle bars 111, 112 while his (her) two feet stepping on the two pedals 1311, 1321 to cause the gear 134 to rotate and thereby drives the blade wheel 137 to rotate through the chain 133. A resistance is formed by the rotation of the blade wheel 137 to offer the user a chance to workout.

Figure 3:
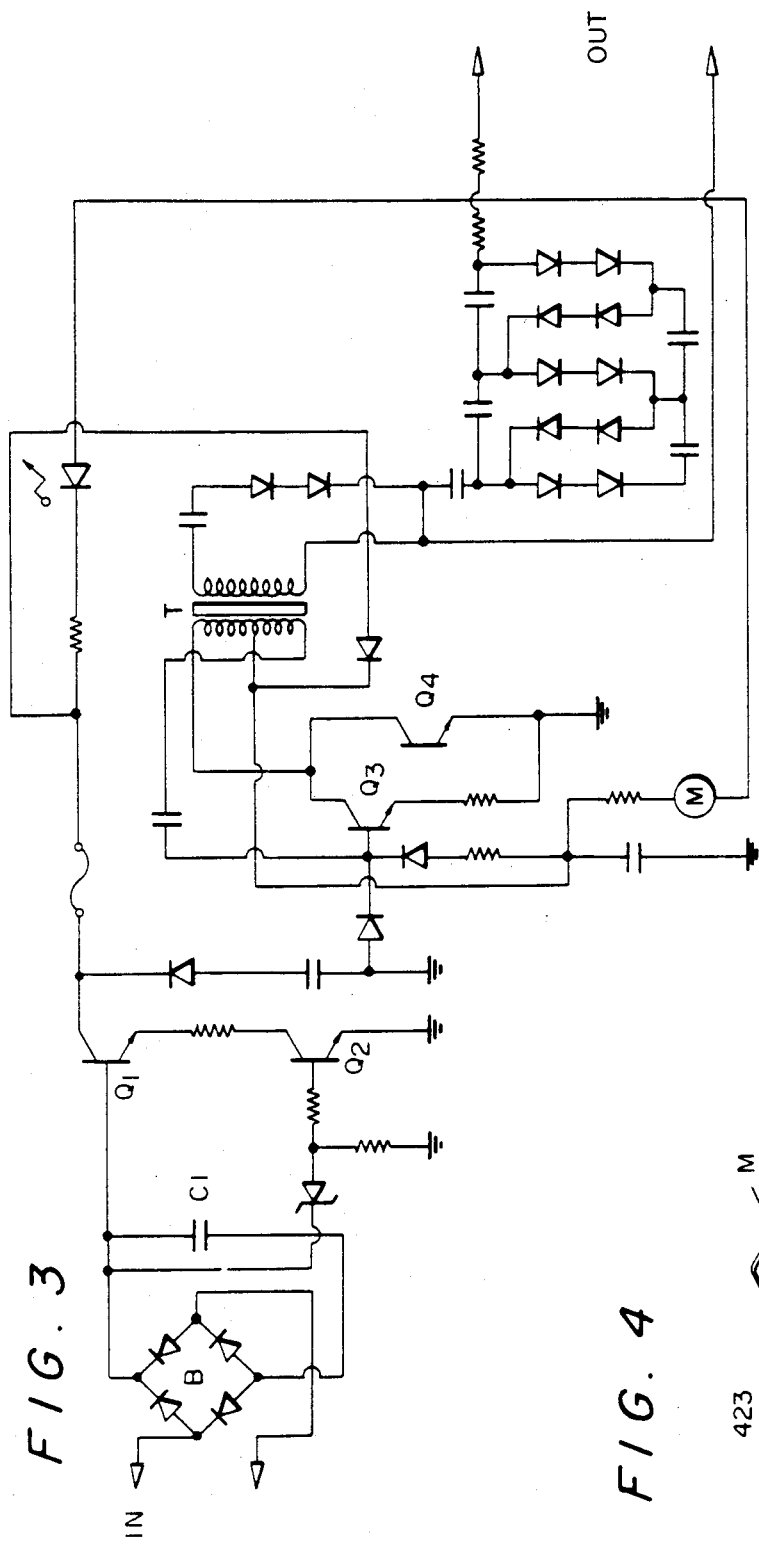
FIG. 3 illustrates the voltage stabilizing and voltage increasing circuit used in the present invention.

The present invention is characterized by a generator 2 provided beside a rubber felloe 1372 of the blade wheel 137. This generator 2 may be the type generally used on a bicycle to provide the power source of bicycle lamps. With rotation of the blade wheel 137, the rubber felloe 1372 drives a pivot axis to rotate and thereby induces the magnetic and coils in the generator 2 to generate power. The power generated by the generator 2 is sent to a circuit board 3 and is voltage-stabilized and amplified through an electronic circuit provided by the circuit board 3 as shown in FIG. 3. The stabilized voltage is then provided as a power source of an ion generator 4 (as shown in FIG. 4) so that the ion generator 4 may be actuated to filtrate the air and generates negative ions to purify the air.

The above-mentioned voltage stabilizing and voltage increasing electronic circuit is formed by a bridge circuit B, a series amplifying circuit formed by two transistors Q1, Q2, a Darlington circuit Q3, Q4, and a transformer T. The DC current generated by the generator 2 passes the bridge circuit B and a capacitor C1 and is filtered and voltage stablized, then passes the series amplifying circuit formed by the transistors Q1, Q2, for the first step voltage amplification, then passes the Darlington circuit formed by transistors Q3, Q4 for the second step signal amplification and is finally voltage increased through the action of the transformer T. By this way, a motor M in the ion generator 4 is driven to rotate, and a fan 421 therein is run to make air flows through the ion generator 4 while the increased voltage is formed in the ion generator 4 to casue the same to generate negative ions.

Figure 4:
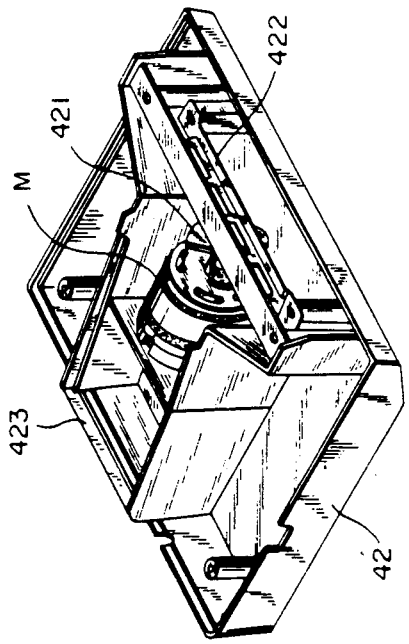
FIG. 4 is a three-dimensional perspective showing part of the ion generator used in the present invention.

The ion generator 4 as shown in FIG. 4 includes a casing 42, an air discharge grill (not shown) on top of the casing 42, a motor M disposed inside of the casing 42 for driving a fan 421, a negative ion generator 422 provided at the front edge of the casing 42, and a filter grill 423 provided at rear side of the casing 42. Power provided by the circuit board 3 is transited to the negative ion generator 422 for the same to generate negative ions. The motor M drives the fan 421 to rotate and thereby causes the air to enter into an air-intake grill (not shown) and pass the filter grill 423, then finally is discharged from the air discharge grill. The discharged air contains negative ions which refresh the air and give users fresh and comfortable feeling.

Figure 5:
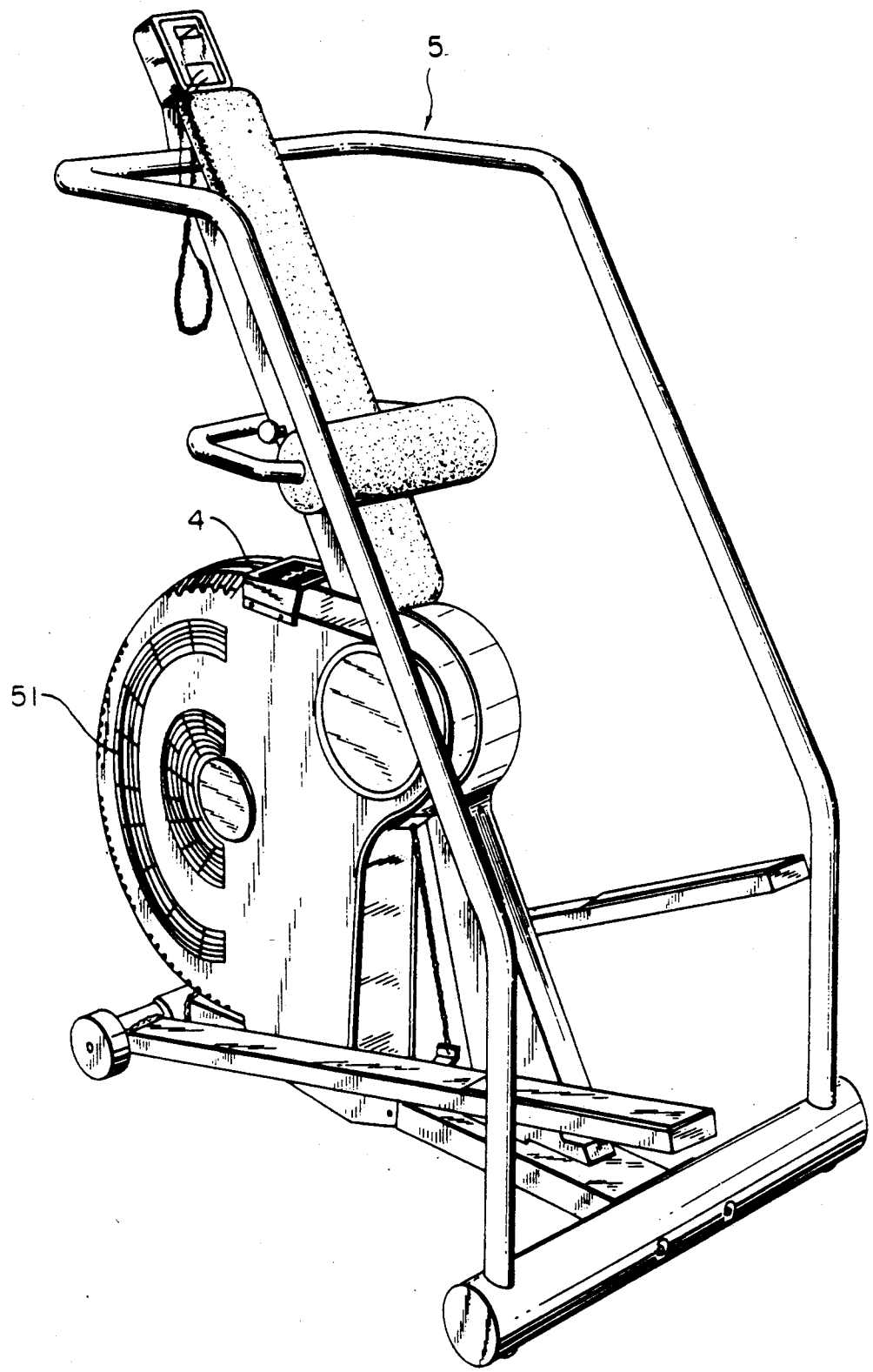
FIG. 5 illustrates another preferred embodiment of the present invention, in the drawing, a stair climbing and air resistance exerciser combined stepper is shown.

The present invention of air resistance exerciser with negative ion generator is not limited to the form of a bicycle type fitness equipment. As shown in FIG. 5, a stair climbing and air resistance exerciser combined stepper 5 has a blade wheel driven to rotate by a rotation mechanism 51. In the rotation mechanism 51, a generator as aforesaid can also be mounted. The voltage of current generated by the generator is stabilizing and increased through a circuit and can be used to actuate the negative ion generator 4 and achieve the purpose of purifying the air.

Figure 6:
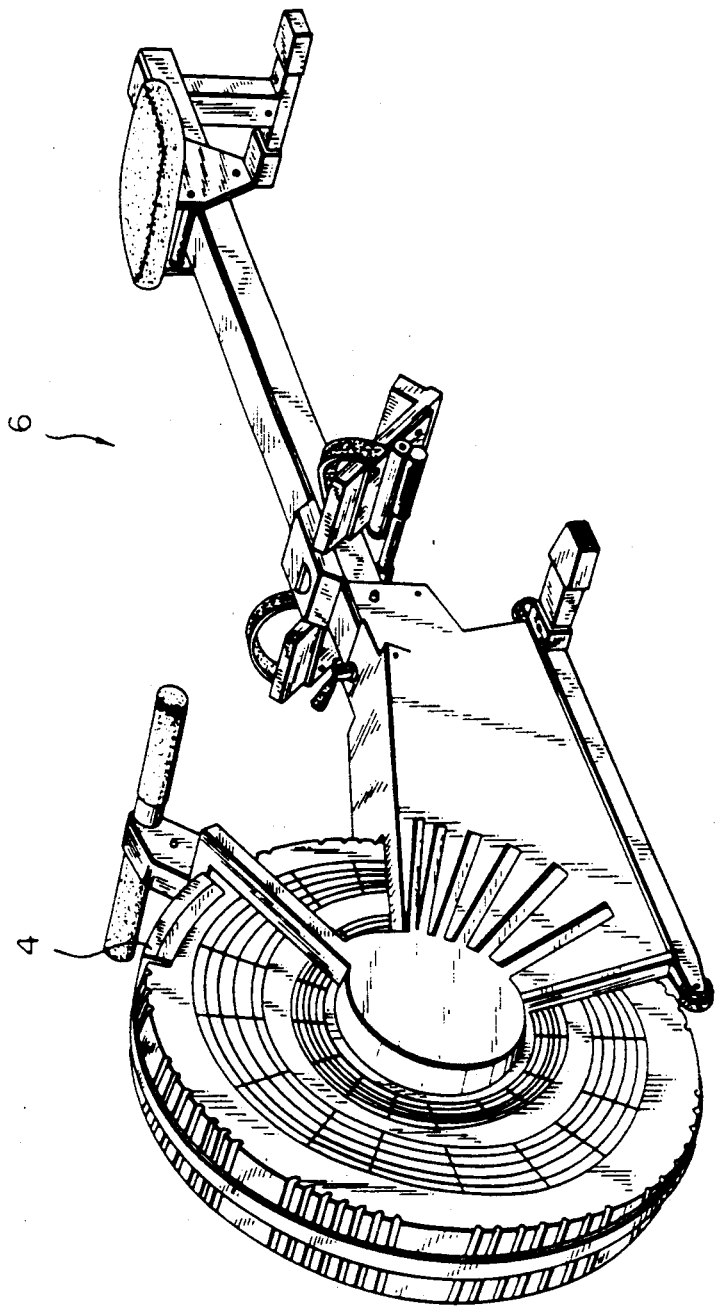
FIG. 6 illustrates another preferred embodiment of the present invention, in the drawing, a rower with an air resistance mechanism of the present invention is shown.

Further, as shown in FIG. 6, a rower 6 or treadmills, etc. all can be provided with a negative ion generator so long as they are in a form of air resistance exercisers. The ion generator 4 is preferrably positioned with its air discharge grill being directly faced to the users.

I claim:

1. An air resistance exerciser with negative ion generator comprising an air resistance exerciser, a generator, a circuit board, and an ion generator; wherein said air resistance exerciser having a rotation mechanism which drives a blade wheel to rotate and thereby provides resistance to an user during exercise; said generator being disposed beside a rubber felloe of said blade wheel at a proper position so that said blade wheel drives said generator to generate voltage, said voltage is stabilized and increased through said circuit board and used as the power source for said ion generator; and wherein said ion generator is disposed on said air resistance exerciser and discharging air to the user, said ion generator being capable of purifying air and discharging negative ions at the same time and, consequently, having the function of eliminating drifting dusts in the air.

2. An air resistance exerciser with negative ion generator as claimed in claim 1, wherein said circuit board includes an electronic circuit comprising a bridge circuit, a double-transistor series amplifying circuit, a Darlington circuit, and a transformer; wherein said voltage generated by said generator passes the bridge circuit and a first capacitor for filtration and voltage stabilization, then passes said series amplifying circuit which is formed by first and second transistors for the first step amplification, and then passes the Darlington circuit which is formed by third and fourth transistors for the second step amplification, finally, the voltage is increased by the transformer.

3. An air resistance exerciser with negative ion generator as claimed in claim 1, wherein said ion generator includes a lower enclosure and an upper enclosure, a motor, a fan and a negative ion generator; wherein said upper enclosure has an air discharge grill on the top surface of said ion generator and an air intake grill on the front portion of said ion generator; said lower enclosure contains said motor which drives said fan to rotate, said negative ion generator disposed at said front portion of said ion generator, and a filter grill provided at the rear side of said ion generator; and wherein said power source from said circuit board actuates the negative ion generator to generate negative ions and drives the motor to turn the fan so that air can be sucked into the ion generator through the air intake grill to be combined with negative ions before passes through the filter grill and being discharged out of the air discharge grill.

* * * * *